(12) United States Patent
Beliaev et al.

(10) Patent No.: US 8,518,690 B2
(45) Date of Patent: *Aug. 27, 2013

(54) PRODUCTION OF BIO-BASED MATERIALS USING PHOTOBIOREACTORS WITH BINARY CULTURES

(75) Inventors: Alex S. Beliaev, Richland, WA (US); Grigoriy E. Pinchuk, Richland, WA (US); Eric A. Hill, Kennewick, WA (US); Jim K. Fredrickson, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 439 days.

This patent is subject to a terminal disclaimer.

(21) Appl. No.: 12/555,631

(22) Filed: Sep. 8, 2009

(65) Prior Publication Data

US 2010/0062483 A1  Mar. 11, 2010

Related U.S. Application Data

(60) Provisional application No. 61/095,413, filed on Sep. 9, 2008, provisional application No. 61/099,380, filed on Sep. 23, 2008.

(51) Int. Cl.

| | |
|---|---|
| *C02F 3/34* | (2006.01) |
| *C12P 39/00* | (2006.01) |
| *C12N 1/00* | (2006.01) |
| *C12N 1/12* | (2006.01) |
| *C12N 1/14* | (2006.01) |
| *C12N 1/20* | (2006.01) |

(52) U.S. Cl.
USPC .......... 435/262; 435/42; 435/243; 435/252.1; 435/254.1; 435/257.1

(58) Field of Classification Search
None
See application file for complete search history.

(56) References Cited

U.S. PATENT DOCUMENTS

| | | | | |
|---|---|---|---|---|
| 6,387,669 | B1 * | 5/2002 | Truex et al. | 435/168 |
| 6,942,998 | B1 * | 9/2005 | Ooteghem | 435/168 |
| 7,393,452 | B2 * | 7/2008 | Tay et al. | 210/601 |
| 7,815,801 | B2 * | 10/2010 | Borg et al. | 210/610 |
| 2006/0163154 | A1 * | 7/2006 | Tay et al. | 210/605 |
| 2009/0325253 | A1 * | 12/2009 | Ascon et al. | 435/163 |

FOREIGN PATENT DOCUMENTS

| | | |
|---|---|---|
| CA | 2005462 A1 | 6/1991 |
| WO | 03093179 A1 | 11/2003 |
| WO | WO 03/093179 | * 11/2003 |
| WO | 2007047805 A2 | 4/2007 |
| WO | 2009133351 A2 | 11/2009 |
| WO | 2009142765 A2 | 11/2009 |

OTHER PUBLICATIONS

O'Reilly, A. M., et al., Defined coimmobilization of mixed microorganism cultures, Enzyme and Microbial Technology, vol. 17, No. 7, 1995, pp. 636-646.

Wikstrom, P. et al., Formation of Alpha Keto Acids From Amino-Acids Using Immobilized Bacteria and Algea, Biotechnology Letters, vol. 4, No. 3, 1982, pp. 153-158.

Dong, Qing-Lin, et al., In situ carbon dioxide fixation in the process of natural astaxanthin production by a mixed culture of *Haematococcus pluvialis* and *Phaffia rhodozyma*, Catalysis Today 98, 2004, 537-544.

Dong, Qing-Lin, et al., Metabolic flux analysis of the two astaxanthin-producing microorganisms *Haematococcus pluvialis* and *Phaffia rhodozyma* in the pure and mixed cultures, Biotechnol. J., 2006, 1, 1283-1292.

* cited by examiner

*Primary Examiner* — Amber D Steele
(74) *Attorney, Agent, or Firm* — A. J. Gokcek; Derek H. Maughan (57) ABSTRACT

A method, device and system for producing preselected products, (either finished products or preselected intermediary products) from biobased precursors or $CO_2$ and/or bicarbonate. The principal features of the present invention include a method wherein a binary culture is incubated with a biobased precursor in a closed system to transform at least a portion of the biobased precursor to a preselected product. The present invention provides a method of cultivation that does not need sparging of a closed bioreactor to remove or add a gaseous byproduct or nutrient from a liquid medium. This improvement leads to significant savings in energy consumption and allows for the design of photobioreactors of any desired shape. The present invention also allows for the use of a variety of types of waste materials to be used as the organic starting material.

10 Claims, 6 Drawing Sheets

PRODUCTION OF BIO-BASED MATERIALS USING PHOTOBIOREACTORS WITH BINARY CULTURES

PRIORITY CLAIM

This application claims priority from provisional patent application No. 61/095,413 filed Sep. 9, 2008 and 61/099,380 filed Sep. 23, 2008 the contents of each are herein incorporated by reference.

STATEMENT AS TO RIGHTS TO INVENTIONS MADE UNDER FEDERALLY-SPONSORED RESEARCH AND DEVELOPMENT

This invention was made with Government support under Contract DE-AC0576RLO1830 awarded by the U.S. Department of Energy. The Government has certain rights in the invention.

BACKGROUND

Rising fuel prices and global climate change concerns have revived the interest in renewable sources of energy. Using solar energy to grow photosynthetic microorganisms is one of the most attractive ways to produce transportation fuels. Successful implementation of biodiesel via seed crops is one example of employing plant-based photosynthesis for fuel production. However, recent assessments of crop-based fuel economy showed that it can lead to food stock deficiency and drive lifecycle emissions of greenhouse gases up through increased land usage. Utilization of photosynthetic microorganisms for primary biomass production has many advantages over growing crops. In particular, arid regions of the western U.S., for example, could be used for large-scale production excluding the competition with food-producing agriculture.

Cultivation of photoautotrophic microorganisms for metabolite and/or biomass production can be accomplished in various types of cultivation systems including open ponds and enclosed bioreactors. Each system has various advantages and limitations. Open ponds, for example, are designed to utilize natural sunlight while most of the enclosed bioreactor systems do require artificial illumination which results in additional energy expenditures. Open pond systems, however, are more prone to fouling by external contamination and are not suited to grow genetically modified organisms. In contrast, enclosed bioreactors provide highly controlled conditions, protection against external contamination, and higher growth rates and biomass/products yields while allowing use of genetically modified strains. Cultivation of photosynthetic organisms is also associated with several general problems which arise from the necessity to deliver $CO_2$ into liquid medium and remove excess $O_2$ produced as a result of photosynthesis in order to maintain desired growth conditions. The current practice is to continuously or periodically purge the system which adds significantly to the operating costs and results in frequent changes of cultivation conditions and reduction in efficiency. Removal of $O_2$ by most other known methods such as by chemical catalysis is typically prohibitively costly. What is needed therefore is a solution that enables continuous operation under controlled conditions such as within an enclosed bioreactor without the need for venting as is required by the prior art. The present invention meets this need.

SUMMARY

The present invention is a method, device and system for producing preselected products, (either finished products or preselected intermediary products) from biobased precursors. The principal features of the present invention include a method wherein a culture consisting of two microorganisms (binary culture), is incubated with a biobased precursor in a closed system to transform at least a portion of the biobased precursor to a preselected product. In some embodiments the binary culture includes at least one oxygenic photoautotroph and at least one aerobic or facultative anaerobic chemoheterotroph. In other embodiments the pairings may include any set of organisms appropriately combined so that the rates of the growth of the two strains of organisms are maintained in an appropriate balance and the internal environment is maintained in a desired condition. This includes but is not limited to pairings of various strains of bacteria, algae, fungi and plant species and combinations thereof. Examples could include but are not limited to pairings of facultative aerobic and anaerobic organisms to produce a self sustaining oxygen/carbon dioxide balance, as well as other combinations wherein the two organisms produce desired or required nutrients or growth enhancing materials. In some embodiments the binary cultures are incubated in a closed chamber and artificially illuminated by variously placed light emitting diodes which are controlled by a control mechanism based upon interaction with a plurality of sensors within the chamber. In other applications the present invention may utilize natural sunlight or ambient light or combinations of ambient and directed light.

In one embodiment of the invention the binary culture includes at least one photoautotroph and at least one chemoheterotroph. In one example this may be selected from any of a variety species including but not limited to *Shewanella* species, *Cyanothece* species, *Synechococcus* species and other species appropriate for the particular necessities of a user. One of the advantages that the present invention provides is that unlike previously used methods for $O_2$ removal/$CO_2$ delivery, this method of cultivation does not need purging of a closed bioreactor with a defined gas phase. In contrast to most prior art practices for $O_2$ removal/$CO_2$ delivery required for microalgae cultivation, the proposed approach accomplishes these tasks simultaneously by inclusion of a compatible heterotrophic microorganism. This method of cultivation does not require sparging of a closed bioreactor with air or other gas mixture/vigorous mixing to deliver $CO_2$/remove produced $O_2$ from liquid medium. This improvement leads to significant savings in energy consumption and allows for the design of photobioreactors of any desired shape to ensure optimal photoautotrophic culture illumination and space usage which will ultimately result in designing more efficient processes with substantial increases in biomass production and/or product generation. Additionally, use of highly reduced organic compounds will help to consume externally added $CO_2$ or a salt of carbonic acid without necessity to remove $O_2$.

The present invention also allows for the use of a variety of types of waste materials to be used as the organic starting material. For example, biosludge produced from sewage water treatment plants or glycerol, a major dead-end byproduct in biodiesel production can be utilized. In addition the present invention can be utilized for the production of microalgae biomass as feedstock for high-quality biofuels (biodiesel and biocrude) that require a minimum of post-production processing. The present invention also enables the design of light-driven processes for bio-$H_2$ production and the production of organic fertilizers, animal feed, and other commodities including but not limited to vitamins, amino acids, antibiotics, or enzymes. The present invention solves the problems associated with the prior art by utilizing binary cultures of paired organism to produce self-sustaining interdependencies that foster the continued growth and development of the organism producing the desired biomass material within the closed system wherein the growth environment can be carefully monitored and maintained. Additionally, more than two cultures may be grown together as necessary. Such an approach provides a cost-efficient way to eliminate problems associated with the prior art methodologies.

In one embodiment of the invention the paired binary cultures are configured to provide $CO_2$ delivery and $O_2$ removal while creating high-value products by utilizing sun light, artificial light or their combination and organic matter (waste or renewables). In one exemplary embodiment a photoautotrophic organism such as a microalga or a cyanobacterium is paired with an aerobic or facultative anaerobic heterotrophic bacterium. The phototrophic oxygenic microorganisms can produce biofuels at a much higher productivity than land plants and can be cultivated in aquatic environments, including seawater, so as to not compete for resources with conventional agriculture. In most prior art systems high costs associated with increasing the mass transfer and by-product ($O_2$) removal limit its use, however in the present embodiment these materials are consumed by an aerobic or a facultative anaerobic heterotrophic bacteria and the desired level of homeostasis within the closed chamber is maintained. This method can be employed by a variety of systems wherein binary cultures of paired organisms cooperatively co-exist to maintain a desired growth environment depending upon the particular needs and necessities of a user.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Various advantages and novel features of the present invention are described herein and will become further readily apparent to those skilled in this art from the following detailed description. In the preceding and following descriptions We have shown and described only the preferred embodiment of the invention, by way of illustration of the best mode contemplated for carrying out the invention. As will be realized, the invention is capable of modification in various respects without departing from the invention. Accordingly, the drawings and description of the preferred embodiment set forth hereafter are to be regarded as illustrative in nature, and not as restrictive.

DETAILED DESCRIPTION OF THE INVENTION

The following description includes the preferred best mode of one embodiment of the present invention. It will be clear from this description of the invention that the invention is not limited to these illustrated embodiments but that the invention also includes a variety of modifications and embodiments thereto. Therefore, the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

As a proof of principle, we have used a binary culture of a photoautotrophic oxygenic cyanobacterium and a heterotrophic facultativeanaerobic bacterium and cultivated them in a non-aerated photobioreactor with addition of organic carbon. During this process, the binary culture produced higher amounts of microalgal biomass without gas sparging (to remove $O_2$ produced during photosynthesis) or additional $CO_2$ injections. While specific examples are described hereafter and provided herein it is to be distinctly understood that the invention is not limited to these described configurations but that a variety of additional configurations and embodiments may be variously and alternatively configured according to the particular needs and necessities of the user. These binary culture systems of phototrophic organisms allow for efficient design and cost effective production processes for directing carbon and nutrients flow from $CO_2$ and waste towards of biofuels: lipids, hydrocarbons and other preselected materials. The examples and descriptions provided herein should therefore be seen as illustrative in nature and not limiting.

To prove this concept various experiments were performed. In one embodiment of the invention a binary culture of a photoautotrophic organism *Cyanothece* sp. strain ATCC 51142 was cultured in association with a facultative anaerobic heterotrophic bacterium *Shewanella* sp. strain W3-18-1 on defined mineral medium which was not supplemented with $CO_2$ or bicarbonate salts as source of carbon. The mineral medium was supplemented with lactate as source of carbon and reducing equivalents to remove the $O_2$. During this process, both organisms in this binary culture were dependent on the metabolism of the other: *Shewanella* sp. W3-18-1 consumed lactate and $O_2$ and produced $CO_2$ and *Cyanothece* sp. ATCC 51142 incorporated the $CO_2$ into the biomass and produced $O_2$. During this process both cultures in the photobioreactor grew without air sparging or addition of supplemental $CO_2$. In the presence of *Shewanella* sp. W3-18-1, *Cyanothece* sp. ATCC 51142 was able to grow at higher rates when compared to single-organism culture under identical conditions with sparging with $CO_2$ and $N_2$.

Figure 1:
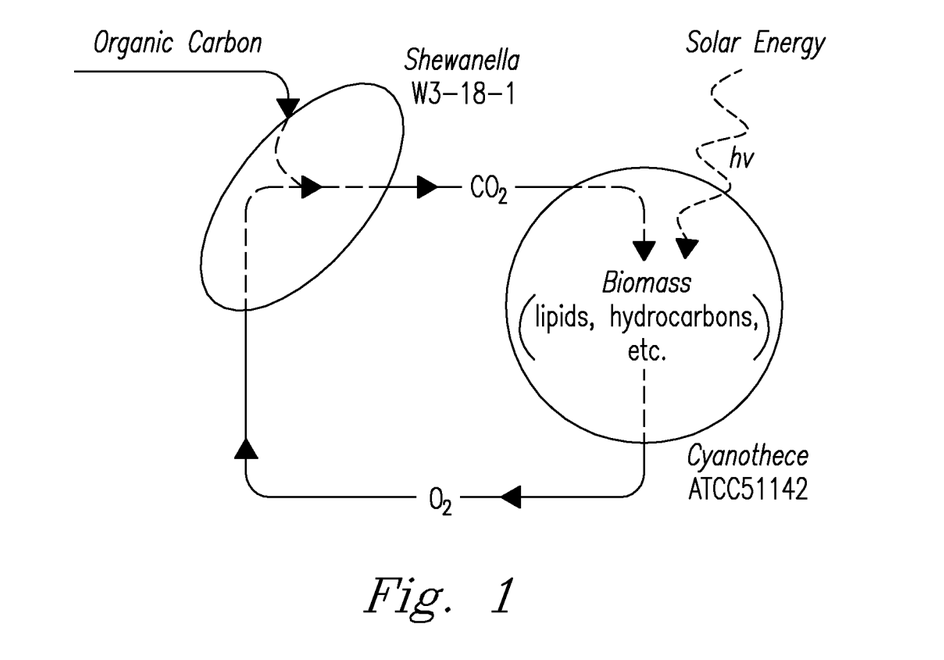
FIG. 1 is a schematic view of the system and process of the present invention.

In another embodiment of the invention an approach was utilized wherein binary photoautotroph-heterotroph cultures were used to spatially separate the processes of photosynthesis and photosynthate conversion into useful products (FIG. 1). This in particular allows for the cultivation of readily-engineered heterotrophic strains for major biotechnology products using $CO_2$ and light instead of commodities such as glucose, sucrose, or other agricultural or synthetic feedstocks. Particularly, phototrophic oxygenic microorganisms that have been genetically or otherwise modified to produce and excrete a soluble organic compound(s) such as glycerol, lactate, pyruvate, acetate or any other organic compound that can be used by a heterotrophic organism as the sole source of carbon and energy to grow and/or synthesize a product of interest. Moreover, $O_2$ as well as carbon and energy source(s) for the heterotrophic organism will be uniformly produced in the liquid culture by phototrophic component of a binary culture, ensuring absence of shock by periodic excess or deficiency of nutrients and oxidants that conventional types of cultivation usually suffer. An aerobic or facultative anaerobic heterotrophic organism will consume $O_2$ produced as the result of photosynthesis, thus dramatically decreasing mass transfer energy expenditure and simplifying photobioreactor design and operation. Additional $CO_2$ produced by heterotroph will be again recycled by phototroph thus ensuring efficient utilization of carbon source(s). The binary culture approach also allows the utilization of various carbon sources ranging from $CO_2$ from power plants to municipal wastes. Because of the robustness of the phototroph-heterotroph association, the binary cultivation provides a novel platform for the development of consolidated bio-processing methods leading to production of carbon-neutral products at reduced economic and energetic costs.

In one set of experiments one embodiment of the system, device and method of the present invention was compared against a prior art system, device and method. A description follows:

Materials and Methods:

Bioreactor:

A New Brunswick Scientific BioFlo 3000 bioreactor with a custom 7.5 Liter vessel was used with a 5.5 Liter working volume. The pH was held at 7.4 with 2 M NaOH and 2 M HCl when necessary. The temperature for all experiments was 30° C. The high agitation experiments were done with 250 rpm, and the low agitation with 50 rpm. Sparging was done with pure air at 2.8 L/min (optimal condition) for the *Shewanella* cultures, with 99% $N_2$ and 1% $CO_2$ for *Synechococcus* sp. PCC 7002 cultures, or with no bubbling for the *Synechococcus* 7002/*Shewanella* W3-18-1 co-cultures. Batches at 50 rpm agitation and 2.8 L/min aeration were also done with pure cultures of *Synechococcus* or *Shewanella* to show effects of low mass-transfer on a pure culture (suboptimal condition 1). Two batches at 50 rpm and 0.5 L/min aeration were done with *Synechococcus* (suboptimal condition 2).

Figure 2:
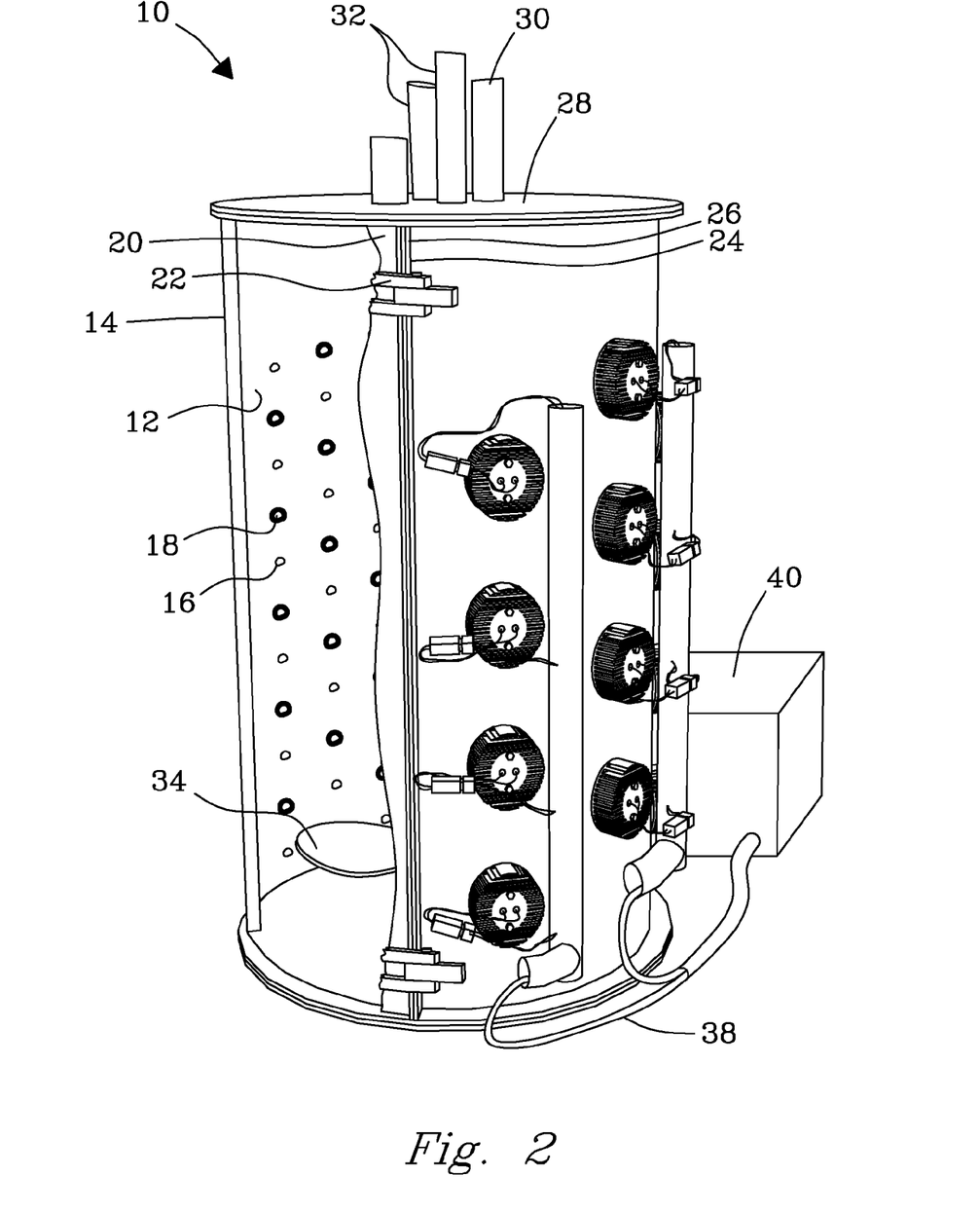
FIG. 2 is an exemplary view of a reactor system of the present invention.

Photobioreactor:

A custom photobioreactor enclosure (developed by Pacific Northwest National Laboratory and shown in FIG. 2) was used for these experiments. This photobioreactor 10 includes a vessel 12 comprised of an outer cylinder 14 made of black anodized aluminum and an inner cylinder 16 made from borosilicate glass. The total height of the vessel 12 in this embodiment was set out at 19.5 inches. The inner diameter was 5.274 inches. The outer diameter (at the flange) was 6.5 inches. While these dimensions were provided in this instance, it is to be distinctly understood that the invention is not limited thereto. However, in the present embodiment it was found that a higher aspect ratio of height to diameter was more effective for enhancing growth within the chamber due to the enhanced ability to allow light to penetrate into the center of the chamber. The bioreactor in this case had no additional ports placed upon the vessel 12. The anodized aluminum shell 14 acts as a mounting point for light emitting diodes (LED) 18 as a heat sink, and as a light shield for ambient light. The black anodized coating of the aluminum absorbs reflected light and acts as an efficient heat-transfer material.

A door 20 on the aluminum shell permits the user to view the inner workings of the photobioreactor 10 as needed. Rubber fasteners 22 securely close the door during normal operation to prevent light from entering or exiting the photobioreactor. Foam rubber seals 24 and rubber gaskets 26 are used on mating surfaces of the photobioreactor 10 to keep it light-tight. The headplate 28 for the photobioreactor is configured to allow probes (to monitor various factors such as pH, DO, level/foaming, and temperature) 30, tubing 32 and an impeller shaft 34 for an agitator to reach the bottom of the vessel. (In this particular example an additional port was added for a $CO_2$ probe for testing purposes but such an addition is not required to allow for proper functioning of the photobioreactor. Similarly an exhaust condenser was included on this embodiment of the application (for testing purposes). In other applications various heat sinks may be added. This is the only photobioreactor design that combines a large working volume, thorough mixing in one common chamber, optimal light delivery, LED lighting, selectable wavelength light, real-time light-intensity measurement and control, modeling of real outdoor lighting patterns and intensities, shielding from ambient room light, pH control, dissolved oxygen control, temperature control, level or foam control, gas mix control, off-gas monitoring, aseptic culturing conditions, and continuous-culture capability in one photobioreactor. This embodiment also provides various advantages in regulating mixed or binary cultures to ensure that appropriate conditions are maintained to support desired rates of growth and preserve and foster desired growth and/or material conversions within said system.

Electronic circuitry 38 directs power from a power supply 40 to the bioreactor 10. A custom control software called Biolume (developed by Derek Hopkins of PNNL) interacts with sensors 40 within photobioreactor and the interactive electronic circuitry to regulate the desired levels of light provided to the photobioreactor. In the experiments described below the light control system was tuned to deliver an identical current to each LED in the system. In the demonstrated embodiment lighting for the photobioreactor is provided by 16 extremely high output illuminators at 630 nm, and 16 at 680 nm. Each illuminator contains 60 high efficiency InGaAlP diode chips (light emitting diodes) made by Marubeni Corporation (Japan). A total of 1,920 light emitting diodes are mounted to the inner wall of the aluminum shell. Each high output illuminator was positioned to be equidistant to adjacent illuminators. The cone of light emitted from each illuminator overlaps with adjacent illuminators to provide even lighting to the reactor surface. In other applications the wavelengths of the LEDs were modified so that half were blue and half were red, the integration of the light control module with the sensors in that application allowed for optimal growth conditions to be established and provided.

Six LI-COR Biosciences quantum sensors (for measuring photosynthetically active radiation) were used to measure light intensities within the photobioreactor. Three sensors measured incident light, and three measured transmitted light. The incident light sensors were mounted facing the LEDs, while the transmitted light sensors were mounted facing the center of the bioreactor. The light control software Biolume allows Proportional Integral Derivative (PID) control of incident or transmitted light intensity. The lighting can respond to a manual set point, or automatically adjust power levels to the LEDs to maintain a set point. In one application light intensity measurements are made by cycling power to just the 630 nm LEDs, then to the 680 nm LEDs, then to both 630 and 680 nm LEDs. Sampling duration and frequency can be adjusted by the user of BioLume. Control of light-intensity can be done from a large table of values allowing the user to reproduce "real outdoor" lighting intensities and timing or create custom lighting schemes. Lights can be turned on, off, or intensity corrected at any time. In the described application a 1 minute light sampling interval (with about 3 seconds total for light measurements) was demonstrated. PID control of light intensities allows the system to predict the future based on the past behavior.

The six quantum sensors were calibrated using a LI-250A Light Meter Quantum/Radiometer/Photometer made by LI-COR Biosciences. The reference light sensor was randomly moved along the inner glass wall of the photobioreactor for 15 seconds while the light meter averaged the light intensities seen during the 15 seconds. The 15 second moving-average light intensities were plotted against the signal produced by the light sensors at varying light intensities to produce a correlation plot. The least-squares best-fit equation was used to translate sensor-signal to light-intensity in $\mu$Einsteins/m$^2$/sec.

A+ medium was used to support organism growth for these experiments and supplemented with lactate as needed. A+ medium contained the following components (concentrations in mM): Tris (8.255 mM), Na$_2$EDTA (0.0806 mM), KCl (8.0483 mM), CaCl$_2$*2H$_2$O (1.8120 mM), MgSO$_4$*7H$_2$O (20.2860 mM), KH$_2$PO$_4$ (0.3670 mM), NaCl (308.0082 mM), NH$_4$Cl (11.7540 mM-20.0 mM), Vitamin B12 (2.95× 10$^{-6}$ mM), H$_3$BO$_3$ (0.5547 mM), MnCl$_2$*4H$_2$O (0.0218 mM), ZnCl$_2$ (0.0023 mM), CoCl$_2$*6 H$_2$O (0.00018 mM), Na$_2$MoO$_4$*2H$_2$O (0.00018 mM), CuSO$_4$*5H$_2$O (0.000012 mM). The pure *Shewanella* cultures were given 45 mM lactate and consumed at most 27 mM of the lactate when grown to the highest density. Subsequent batches of the co-culture were given 25 mM lactate to avoid having excess lactate in the medium and were grown to lower biomass concentrations as measured by optical density. No lactate was added for batches of pure *Synechococcus* because preliminary experiments showed that lactate neither was consumed by *Synechococcus* nor affected its growth otherwise.

*Shewanella* W3-18-1 was grown in a 5.5 L batch at 250 rpm with 2.8 L/min sparging with air. Most of the culture was removed and replaced with fresh medium before growing the cells to the same final optical density. Reproducibility of the duplicate batches was shown before decreasing the agitation speed to 50 rpm. Growth rates and biomass yields were analyzed at the lower agitation speed.

*Synechococcus* sp. PCC 7002 was grown in batch phase for three replicate batches at 250 rpm and 2.8 L/min sparging rate with 99% N$_2$ and 1% CO$_2$. Reproducibility of replicate cultures was evaluated and then the agitation was decreased to 50 rpm for replicate batches. The effects of 50 rpm agitation on growth-rate and biomass yield were evaluated and then the culture was allowed to grow to late log-phase for replicate batches using 0.5 L/min bubbling. The late log-phase batches were done to show that all other samples were considered mid-log phase. The biomass yield and growth-rate were determined and then the culture was diluted with fresh medium in preparation for co-culture growth with *Shewanella* W3-18-1. Lactate was added to the medium to act as a source of carbon and energy for *Shewanella* and carbon for *Synechococcus*.

*Shewanella* W3-18-1 and *Synechococcus* 7002 were grown together in batch-phase. *Shewanella* W3-18-1 used lactate to produce CO$_2$ needed by *Synechococcus* 7002. In turn, *Synechococcus* produced O$_2$ needed by *Shewanella* W3-18-1 to oxidize lactate. After diluting the culture with fresh medium, the dissolved CO$_2$ concentration in the medium was very low as measured by a dissolved CO$_2$ probe. To speed up growth of the co-culture on the 1$^{st}$ batch after inoculation of both species, a small amount of sodium bicarbonate was added (about 0.5 mM). Subsequent batches of co-culture did not require supplementation with bicarbonate.

Results

Figure 4:
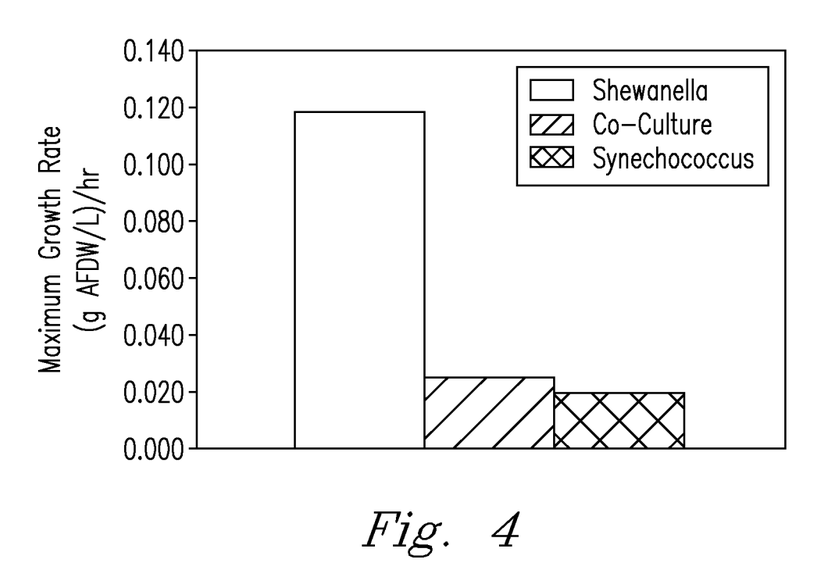
Figure 5A:
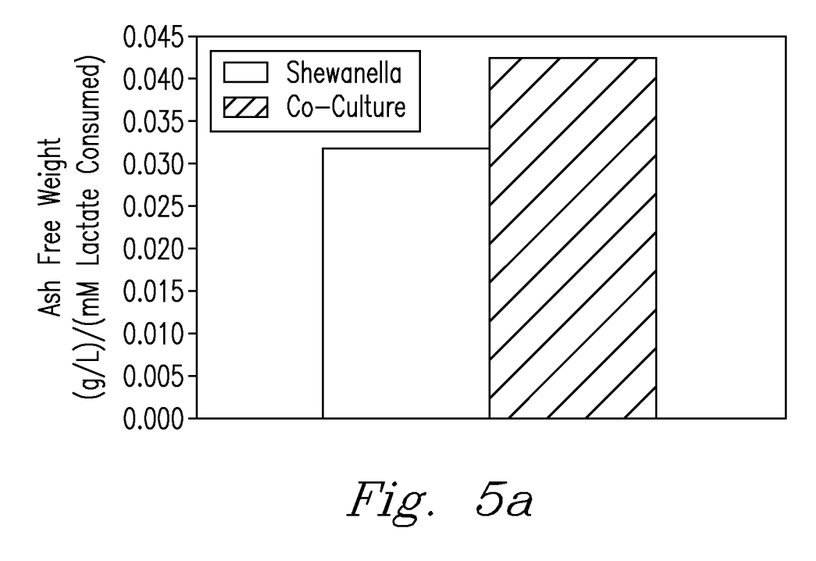
FIGS. 5a and 5b shows the efficiency of the use of lactate in the various tested cultures.
Figure 5B:
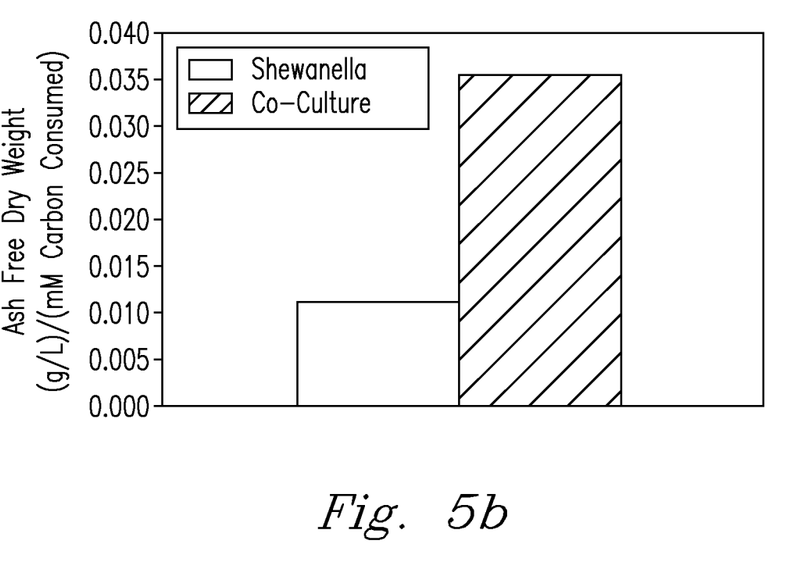

*Synechococcus* grew at the same rate at 250 rpm and at 50 rpm agitation as long as 2.8 L/min gas-addition was used. However, the growth-rate decreased slightly when 50 rpm agitation and only 0.5 L/min aeration was used. Mass transfer through the high-aspect-ratio reactor (described in paragraph 23) was much more efficient than would be expected of a lower aspect ratio reactor with a shorter path-length for gas-exchange. The impact of mass transfer changes (agitation and aeration) have been much more obvious in a lower aspect ratio reactor as our previous experiments with *Shewanella* showed. The maximum growth-rate of pure *Synechococcus* was nearly the same as the co-culture of *Synechococcus* and *Shewanella*. This is because the co-culture is rate-limited by the growth of *Synechococcus* as the result of both strains tight metabolic coupling. The lag phase of growth of *Synechococcus* was longer than the lag phase for the co-culture (see FIG. 3), and *Shewanella* W3-18-1 grew faster than the co-culture or pure *Synechococcus* (see FIG. 4) as cyanobacteria generally has lower growth rates than aerobically grown heterotrophs under optimal conditions. However, *Shewanella* did not use lactate as efficiently as the co-culture (see FIG. 5a). The co-culture used lactate 25% more efficiently than *Shewanella* alone because *Synechococcus* used CO$_2$ that was produced by pure *Shewanella* cultures. Analysis of culture filtrates for organic acids revealed that lactate was not used fully by coculture. Aacetate and sometimes formate (products of partial lactate oxidation by *Shewanella*) were found in the coculture environment. When growth yield was calculated per mole of carbon used we found that co-culture converts carbon to biomass 3.2 times better than the pure *Shewanella* culture (see FIG. 5b).

Figure 3:
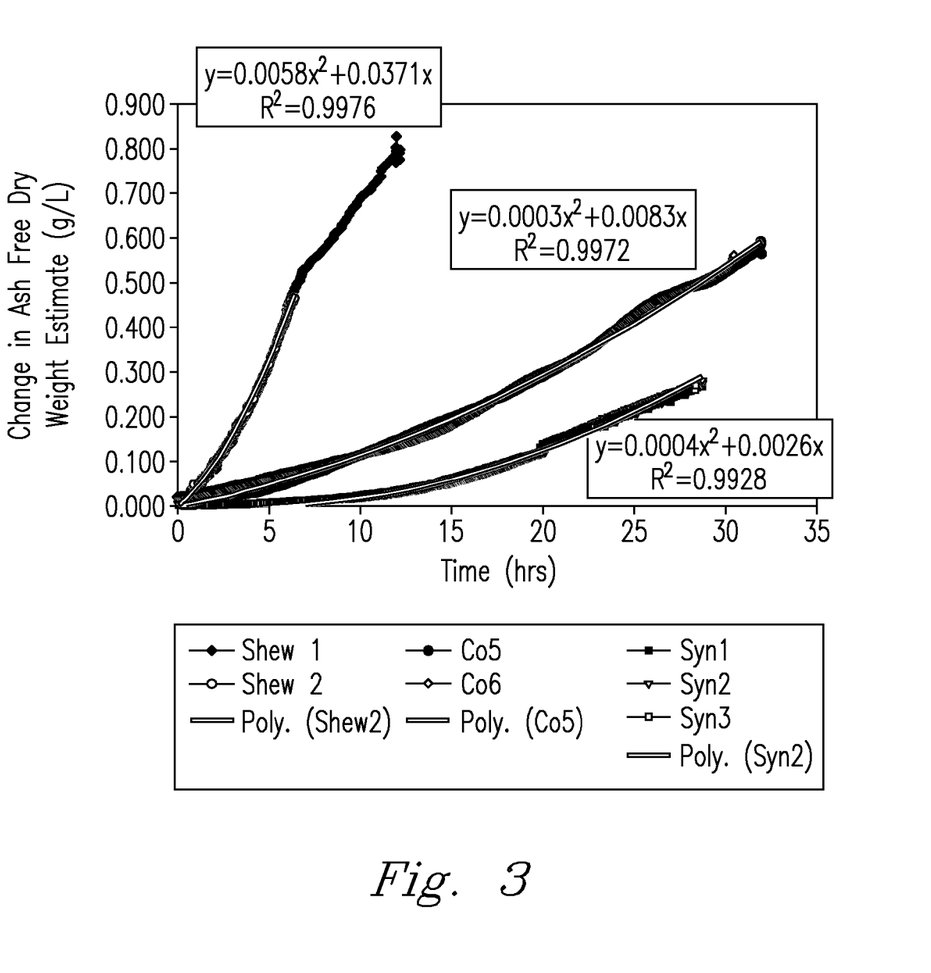
FIGS. 3 and 4 are charts showing the independent growth phases of *Synechococcus* and *Shewanella* examples as compared to the binary culture.

*Shewanella* grew much better than expected at lower agitation (50 rpm). Again, this is due to the unusually high aspect ratio of the used bioreactor. The 50 rpm culture did become O$_2$-limited as was indicated by the red color of the culture due to the production and extracellular localization of cytochromes and accumulation of acetate. The biomass yield of the 50 rpm culture of *Shewanella* was much lower than the 250 rpm culture by ash-free dry weight. *Shewanella* produced about 0.8 g/L of ash-free dry weight in a 12 hour growth period with 250 rpm (see FIG. 3). This biomass concentration exceeded what was produced by the co-culture or *Synechococcus* in 30 hours (FIG. 3).

Figure 6:
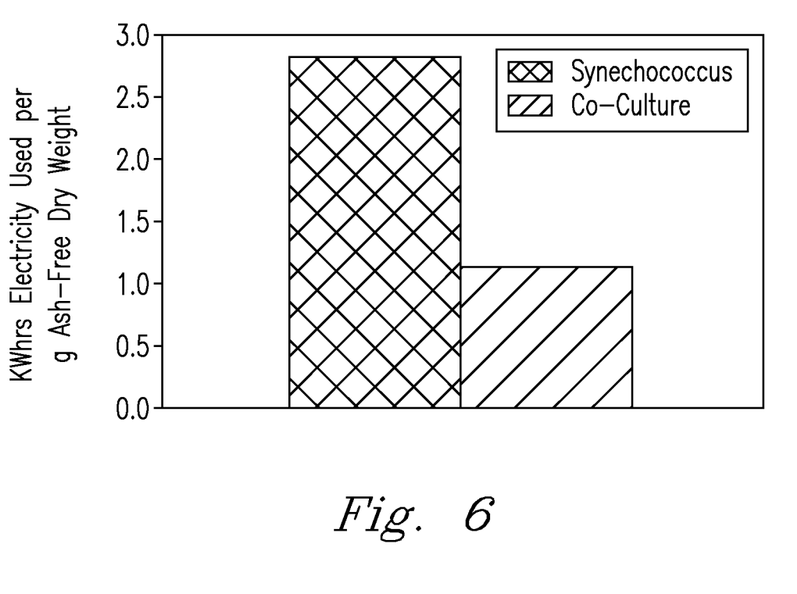
FIG. 6 shows the results of light testing of the *Synechococcus* culture.

The co-culture of *Shewanella* and *Synechococcus* grew at about the same maximum growth rate as pure *Synechococcus* (on an ash-free dry weight basis). However, the co-culture used light 2.5 times more effectively than the pure *Synechococcus* culture (see FIG. 6). In other words, the biomass yield as ash-free dry weight for a given amount of light was 2.5 times as high for the co-culture as the pure *Synechococcus* culture. Obviously, the growth rate of the coculture was limited by growth rate of *Synechococcus* (see [0032]) as the result of tight metabolic coupling of two species.

The packed cell volume analysis showed that a co-culture of *Shewanella* and *Synechococcus* had a stable ratio of about 1:1 by cell volume. The amount of *Synechococcus* was always slightly higher that *Shewanella*, with *Synechococcus* to *Shewanella* ratios from 1.03:1 to 1.3:1. A packed cell volume sample that was 43.45% (+/−0.76) *Shewanella* and 56.55% (+/−0.76) *Synechococcus* by volume was shown to have a percent by mass of 43.51% *Shewanella* and 56.49% *Synechococcus*. This means that the density of the cell pellets in g/L is equal for *Synechococcus* and *Shewanella*. We can therefore relate the packed cell volume analysis directly to cell mass (ash free dry weight) by multiplying the fractional-share of the cell-volume by the combined ash-free dry weight.

The presence of products of not complete lactate oxidation described in paragraph [0032] was the consequence of *Shewanella* growing faster than *Synechococcus* and therefore it exhausted $O_2$ faster than *Synechococcus* could produce it. As the result, *Shewanella* growth was limited by $O_2$. Under $O_2$ limitation *Shewanella* is known to convert part of lactate into acetate and additionally can accumulate some formate; both these compounds cannot be used by *Synechococcus*, therefore decreasing its growth and $O_2$ production rate. Hence, the process may become self-fading unless some external $O_2$ or $CO_2$/bicarbonate is added. This conclusion is supported by the following experiments. Uncontrolled batches of *Shewanella, Synechococcus*, and binary co-cultures of these bacteria were grown at room temperature (23-24° C.) in sterile Roux bottles (total volume 1 L) without gas sparging and mixing of cultural liquid. Bottles were illuminated with cool white light at 55 µEinsteins/$m^2$/sec. In the first set of experiments 0.6 L of A+ medium (supplemented with 9 mM lactate in case of pure *Shewanella* or binary cultures) was added, therefore leaving 0.4 l of air present in the headspace. Both pure cultures did not produce significant growth for more than 250 hours, whereas binary culture fully used lactate for 120 hours. Biomass yield of co-culture was 6 times higher than yield of pure *Shewanella* produced in controlled aerated bioreactor (see FIG. 3a) and was 40 g of ash-free dry weight/mol of lactate carbon. Toward the end of active growth of binary culture most of the cells precipitated and formed a pellet on the bottom of the Roux bottle. This precipitation can be used as the way to concentrate biomass in the process of growth by proper cultivation chambers design without necessity to centrifuge whole fermentation broth, therefore potentially leading to significant additional energy savings on downstream processing. Additionally, packed cell volume analysis showed that co-culture of *Synechococcus* and *Shewanella* grown with additional $O_2$ influx from the bottle headspace had a ratio 5:1 by cell volume, which means that *Synechococcus* made 5 times more biomass per lactate used that it did in binary culture bioreactor runs without external $O_2$ influx (see [0035]). In the second set of experiments the Roux bottles were filled with 960 ml of media. These experiments yielded no growth for pure *Synechococcus* and *Shewanella* cultures; result for binary culture was comparable with those obtained in photobioreactor experiments. The overall binary culture growth limitation with $O_2$ caused by higher *Shewanella* growth rate and incomplete lactate oxidation can be overcome as follow. (1) Our previous experiments with *Shewanella* showed that deletion of ackA gene encoding for acetate kinase abolished incomplete lactate oxidation and acetate excretion under $O_2$ limitation. All lactate was converted into $CO_2$ and biomass, their ratio depended on the level of $O_2$ supply. (2) Alternatively, addition of $CO_2$ or bicarbonate (see [0031]) will enhance specific rate of $O_2$ production by cyanobacteria in the initial stage of cultivation and as the result increase robustness of binary culture and final biomass production, yield, and degree of organic carbon source assimilation by the binary culture.

Figure 7:
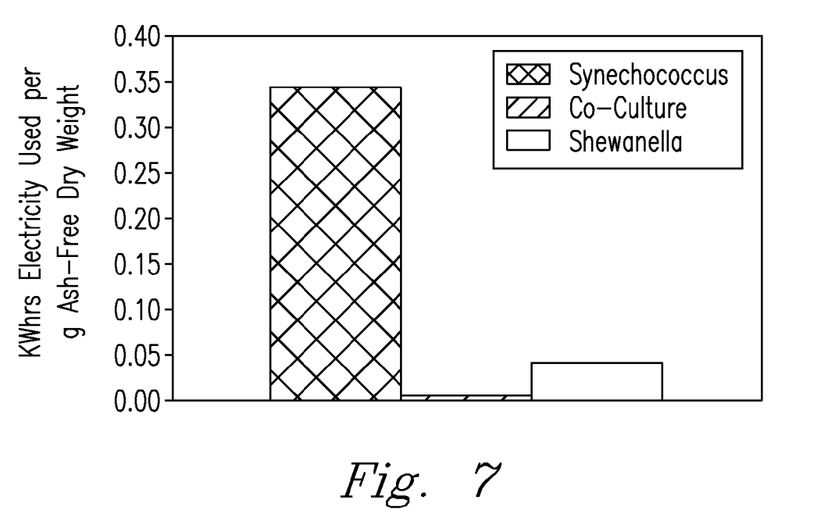
FIG. 7 shows the quantity of electricity used for agitation and gas sparging per unit biomass.

The graph of electricity used (KWhrs) for illumination, sparging, and agitation per gram of ash-free dry weight (see FIG. 6) shows that *Synechococcus* required the greatest investment for the smallest return; whereas, *Shewanella* produced the greatest amount of biomass for the smallest input of electricity. This is because *Shewanella* did not require illumination, which was one of the costliest expenditures for electricity in this experiment. Use of sunlight will significantly reduce energy expenditures on binary culture illumination as well as optimization of lighting conditions and overall process design. The amount of electricity used for agitation and sparging per unit biomass (grams of ash-free dry weight) was highest for pure *Synechococcus* and lowest for the co-culture {57 times lower} (see FIG. 7). It should be noted that experiments conducted in Roux bottles used neither sparging nor mixing therefore potentially driving energy expenditures for these purposes almost to nothing. Since *Shewanella* required both bubbling and agitation, it required about 7 times more electricity per unit biomass as the co-culture. Thus, binary cultures not only provide advantage in relation to efficiency because venting or sparging is no longer needed. There are also substantial cost improvements because there is no need for aerating the mixtures and off-gas purification, the last absolutely necessary in the industrial environments.

Unlike other methods described in the prior art the proposed approach accomplishes $CO_2$ delivery/$O_2$ removal simultaneously with the process of biomass/product biosynthesis. This method of cultivation does not need sparging of a closed bioreactor with air or other gas mixture/vigorous mixing to deliver $CO_2$/remove produced $O_2$ from liquid medium. This improvement leads to significant savings on energy consumption to accomplish these tasks. It also allows designing photobioreactors of any desired shape to ensure optimal illumination and space usage. Use of highly reduced organic compounds (for example wasted fats) in some cases will help to consume externally added $CO_2$ or bicarbonate without necessity to remove $O_2$ As source of organic matter many types of waste materials can be used, for example biosludge produced from sewage water treatment plants or starch solutions generated as the result of industrial potatoes processing that are typically wasted. Some of these materials may also be a cheap source of other nutrients such as N, P, and S sources.

In addition to the organisms previously described, a variety of other organism pairings are envisioned. These include pairs of *Synechococcus* sp. PCC6038+*Shewanella oneidensis* MR-1 and *Cyanothece* ATCC 51142+*Shewanella* sp. W3-18-1. Other possible candidates from phototrophic side include microorganisms that are able to grow autotrophically by using $CO_2$ as the source of carbon, light as the source of energy, and water as source of electron, i.e. carry water splitting and produce oxygen: Examples of such organism include but are not limited to various types of cyanobacteria: nitrogen fixing, both single cell (e.g. *Cyanothece*, some species belonging to *Synechococcus*) and filamentous (e.g. *Trichodesmium, Anabaena, Nostoc*), and non nitrogen fixing belonging to single cell (e.g. *Synechocystis*, some species belonging to *Synechococcus*) and filamentous e.g. *Arthrospira* (former *Spirulina*) as well as various genetically modified strains of these organisms. Other examples include microalgae: e.g. *Haematococcus pluvialis, Clamydomonas* etc., as well as various genetically modified strains. Any heterotrophic obligatively aerobic or facultative anaerobic microorganism, belonging to archaea, bacteria, or eukaryotes, that are able to oxidize organic compounds to $CO_2$ using $O_2$ as electron acceptor, and use organic compounds for growth and/or biosynthesis of product of interest may also be utilized examples of such materials include: *E. coli, Corynebacterium glutamicum, Saccharomyces cerevisiae* and the like.

The present invention core forms an economically attractive way to create a variety of biobased products including but not limited to biomass; $H_2$; organic fertilizers; biodiesel and biocrude oil; ethanol; amino acids; vitamins; antibiotics; polysaccharides and fine chemicals, for example D- and L-lactate as polylactates precursor. These methodolgies may also be utilized in a variety of other different ways including but not limited to biosludge and other organic wastes utilization in economically sound way. In addition other embodiments may provide other possibilities and potentials such as the ability to regulate $CO_2$ production/$O_2$ removal or $CO_2$ consumption/$O_2$ removal at desired rates.

While various preferred embodiments of the invention are shown and described, it is to be distinctly understood that this invention is not limited thereto but may be variously embodied to practice within the scope of the following claims. From the foregoing description, it will be apparent that various changes may be made without departing from the spirit and scope of the invention as defined by the following claims.

What is claimed is:

1. A method for producing preselected products from biobased precursors said method characterized by incubating a culture in a single closed reactor vessel said culture comprising a metabolically paired combination of at least one phototrophic culture which produces biobased precursors and $O_2$ and at least-one heterotrophic strain to transform at least a portion of said biobased precursor to a preselected product without sparging or adding gasses into said vessel.

2. The method of claim 1 wherein said culture comprises at least one strain of bacteria and one strain selected from the group consisting of algae and fungi.

3. The method of claim 1 wherein said closed vessel is at least partially artificially lighted.

4. The method of claim 3 wherein said closed vessel includes a chamber having sensors positioned therein.

5. The method of claim 4 wherein said sensors are operatively interconnected to an artificial lighting system.

6. The method of claim 1 wherein said culture includes a *Shewanella* species.

7. The method of claim 1 wherein said culture includes a *Cyanothece* species.

8. The method of claim 1 wherein said culture includes a *Synechococcus* species.

9. The method of claim 1 wherein said biobased precursor is not a feedstock material.

10. The method of claim 9 wherein said biobased precursor is a waste material.

* * * * *